United States Patent [19]

Hahn

[11] Patent Number: 5,061,692

[45] Date of Patent: Oct. 29, 1991

[54] METHODS AND COMPOSITIONS FOR THE TREATMENT OF NON-IGE-MEDIATED DISEASES

[75] Inventor: Gary S. Hahn, Cardiff by the Sea, Calif.

[73] Assignee: Immunetech Pharmaceuticals, San Diego, Calif.

[21] Appl. No.: 382,623

[22] PCT Filed: Dec. 9, 1987

[86] PCT No.: PCT/US87/03222

§ 371 Date: Nov. 23, 1989

§ 102(e) Date: Nov. 23, 1989

[87] PCT Pub. No.: WO88/04177

PCT Pub. Date: Jul. 16, 1988

Related U.S. Application Data

[63] Continuation-in-part of Ser. No. 939,927, Dec. 9, 1986, Pat. No. 4,816,449, which is a continuation-in-part of Ser. No. 899,891, Aug. 25, 1986, abandoned, which is a continuation of Ser. No. 824,945, Feb. 3, 1986, Pat. No. 4,628,045, which is a continuation of Ser. No. 746,175, Jun. 18, 1985, abandoned, which is a continuation-in-part of Ser. No. 522,601, Aug. 12, 1983, abandoned.

[51] Int. Cl.[5] .......................... A61K 37/02; C07K 7/06
[52] U.S. Cl. ........................................................ 514/17
[58] Field of Search ............................................ 514/17

[56] References Cited

U.S. PATENT DOCUMENTS

| 4,161,552 | 7/1979 | Hamburger | 530/330 |
| 4,171,299 | 10/1979 | Hamburger | 530/330 |
| 4,579,840 | 4/1986 | Hahn | 530/330 |
| 4,628,045 | 12/1986 | Hahn | 530/330 |
| 4,683,292 | 7/1987 | Hahn | 530/328 |
| 4,686,282 | 8/1987 | Hahn | 530/327 |
| 4,692,511 | 9/1987 | Hahn | 530/328 |
| 4,816,449 | 3/1989 | Hahn | 514/17 |

OTHER PUBLICATIONS

Cohen, et al., Ann. Allergy, 52(2):83–86 (1984).
Hahn, et al., J. Allerg. Clin. Immunol., 85(1 part 2):298 (1990).
Tzehoval, et al., Springer Semin. Immunopathol, 2:205–214 (1979).

Primary Examiner—Lester L. Lee
Attorney, Agent, or Firm—Lyon & Lyon

[57] ABSTRACT

Methods and compositions for the treatment of non-IgE-mediated inflammatory disease conditions utilizing the peptide Asp-Ser-Asp-Pro-Arg, or derivative thereof are disclosed.

10 Claims, No Drawings

METHODS AND COMPOSITIONS FOR THE TREATMENT OF NON-IGE-MEDIATED DISEASES

The present application corresponds to, and claims the benefit of, international application number PCT/US87/03222, filed Dec. 9, 1987, and is a continuation-in-part of U.S application Ser. No. 939,927, filed Dec. 9, 1986 and now U.S. Pat. No. 4,816,449. Ser. No. 939,927 is a continuation-in-part of Ser. No. 899,891 (filed Aug. 25, 1986 and now abandoned), which is a continuation of Ser. No. 824,945 (filed Feb. 3, 1986 and now U.S. Pat. No. 4,628,045), which is a continuation of Ser. No. 746,175 (filed June 18, 1985 and now abandoned), which is a continuation-in-part of Ser. No. 522,601 (filed Aug. 12, 1983 and now abandoned). The entire disclosures of these applications are incorporated herein by reference.

BACKGROUND OF THE INVENTION

The immune system of humans and animals normally functions to protect its host from infectious organisms or from cancerous transformation by host cells. In many instances however, the immune system manifests a response that itself results in considerable damage to otherwise healthy cells and organs. Such over-reactivity of immune responsiveness is responsible for many serious conditions or diseases including allergies and autoimmune diseases.

In order to classify the processes by which the immune system produces cellular damage, immunologists have divided immune responses into four broad classes (Type I, II, III and IV) (Roitt, I. M., et al., *Immunology*, C. V. Mosby, N. Y., 1985, p. 19.1).

Type I responses are also called immediate hypersensitivity reactions and include those diseases which produce the symptoms classically associated with "allergies" or the "allergic syndrome" including allergic rhinitis (hay fever), allergic asthma, allergic conjunctivitis and allergic reactions to insect stings or foods. These conditions are characterized by a rapid clinical manifestation of allergic symptoms within minutes after exposure to an antigen (allergen) to which the subject has been previously sensitized.

In order for Type I hypersensitivity to occur, a specialized sequence of events within mast cells and basophils must be triggered by immunoglobulin E (IgE) antibodies that have been manufactured within the body. In this process, IgE directed toward an antigen (allergen) must bind to receptors on mast cells and basophils which specifically bind to the Fc region of IgE. Mast cells and basophils that have allergenspecific IgE bound to them are considered to be sensitized or "armed" for subsequent exposure to allergen. Should allergen be introduced into the local environment of the mast cells or basophils, the cells are automatically stimulated or "triggered" to release histamine and other vasoactive chemicals which produce the familiar "allergic symptoms" characteristic of allergic disease.

The hypersensitivity states characterized by types II, III and IV hypersensitivity are distinguished from type I hypersensitivity by many distinct and diverse features.

Type II hypersensitivity occurs when IgG or IgM antibodies bind to antigens located on the surfaces of cells. Such binding is mediated by the antibodies' Fab arms which contain specific structures that recognize cell surface antigens. Upon binding, the Fc regions of IgG or IgM interact with the complement system (a family of inflammatory and cell-killing molecules) or immune system "killer" cells bearing IgG or IgM Fc receptors. Some examples of diseases in which type II hypersensitivity reactions predominate include transfusion reactions, hemolytic disease of the newborn, autoimmune hemolytic anemias, hyperacute graft rejection, Goodpasture's syndrome, myesthenia gravis and other conditions.

Type III hypersensitivity is produced when complexes or aggregates of antibodies (usually IgG or IgM) and soluble antigens form in abnormally large amounts and activate the complement inflammatory system. Some examples of diseases in which type III hypersitivity reactions are pathogenically important include systemic lupus erythematosis, rheumatoid arthritis, polyarteritis and other forms of vasculitis, fibrosing alveolitis and many infectious diseases, especially bacterial endocarditis, hepatitis and malaria.

Type IV hypersensitivity (delayed-type hypersensitivity), by contrast to the other three hypersensitivity reactions, is triggered primarily by T cells having specialized T cell receptors able to recognize and bind to the specific sensitizing antigen on a cell's surface. Upon reexposure to an antigen, T cell receptor molecules bind to the antigen and trigger a complex series of events that result in secretion of lymphokines and other regulatory molecules that recruit new cells leading ultimately to the destruction of the antigen-bearing cell. Delayed type hypersensitivity, as its name implies, has a delayed onset of inflammation that ranges from about 24 hours to several days after reexposure to the sensitizing antigen. Diseases in which type IV hypersensitivity is believed to play an important pathogenic role are frequently termed "T-cell mediated" to reflect the unique role played by the T-cell in recognizing the sensitizing antigen. These diseases include multiple sclerosis, rheumatoid arthritis, juvenile onset diabetes mellitus, ulcerative colitis, and regional enteritis (Crohn's disease), among others.

An important principle that distinguishes type I hypersensitivity (allergy) from the other hypersensitivity states discussed above is that the allergic inflammation begins within minutes after allergen exposure. By contrast, other hypersensitivity states exhibit inflammation only after hours to days following reexposure to the sensitizing agent.

A second important principle that distinguishes type I hypersensitivity from other hypersensitivity states is the source of the sensitizing agent In type I hypersensitivity, the sensitizing agent (allergen) is not a part or component of the host body. Instead, the allergen is a substance found outside of the host body that is later introduced into the body by exposure to the environment. Types II, III and IV hypersensitivity, by contrast, may have immune responses directed towards antigens located on cells and molecules that are normal constituents of the body. Such immune responses toward normal constituents of the body are termed "autoimmune diseases" and constitute a medically important class of diseases distinct from allergic diseases.

A third important principle that distinguishes type I hypersensitivity from other hypersensitivity states is the degree to which cell killing occurs. In type I hypersensitivity, the IgE-mediated triggering reaction which causes the release of vasoactive allergic mediators does not result in the death of the releasing mast cell or basophil Instead, the "trigger" reaction is the result of an active secretory process that may recur after a length of time. Similarly, the effect of the vasoactive allergic mediators on surrounding cells is regulatory, not cytotoxic. Allergic mediators serve to increase the permeability of small blood vessels and activate a variety of vasoregulatory and immunoregulatory processes that do not normally result in cell death. Types II, III and IV hypersensitivity, by contrast, have as a principal function cell killing reactions which normally lead to the destruction of infectious agents or cancer cells.

In 1975, Hamburger reported that a pentapeptide with a sequence derived from the constant domain of human IgE could inhibit a local cutaneous allergic reaction (Prausnitz-Kustner) by approximately 90% (Hamburger, R., Science 189:389, 1975; U.S. Pat. Nos. 4,171,299 and 4,161,522). This pentapeptide, Asp-Ser-Asp-Pro-Arg, is known as Pentigetide The peptide has been shown to inhibit systemic allergic disease in humans after injection by the subcutaneous route.

SUMMARY OF THE INVENTION

The present invention discloses the surprising finding that Pentigetide not only has antiallergic (antitype I hypersensitivity) activity as specified by U.S. Pat. Nos. 4,161,522 and 4,171,299, but also have additional, unexpected medically useful properties as well. By contrast, the two cited patents disclose only that Pentigetide ha s antiallergic (anti-type I hypersensitivity) activity. As will be presented in the present application, allergies or the "allergic syndrome" are medical conditions clearly distinct from the new disease applications disclosed in the present invention Specifically, Pentigetide has a general anti-inflammatory activity in addition to its antiallergic anti-inflammatory activity. The anti-inflammatory activity described in the present invention is broad and extends to diseases and conditions other than IgE-mediated disease conditions.

Therapeutic antiallergic agents only rarely exhibit therapeutic activity in the non-allergic diseases and conditions disclosed in the present invention. For example, the commonly used therapies for allergic disease include antihistamines, cromolyn sodium, immunotherapy, alpha adrenergic agonists (vasoconstrictors), beta adrenergic agonists (bronchodialators), methylxanthine preparations (e.g., theophylline), mucolytics, expectorants and steroids. Of these therapeutics, only steroids exhibit anti-inflammatory activity in allergic and non-allergic diseases.

More specifically, Pentigetide is able to suppress inflammation caused by a range of inflammatory reactions common to type II, III and IV hypersensitivity reactions and inflammatory reactions produced by the application or exposure of the body or its parts to irritating or inflammation-producing agents.

This surprising discovery strongly suggests that Pentigetide is useful in the treatment of a variety of non-allergic (non-type I hypersensitivity) conditions or diseases previously discussed. It additionally suggests that Pentigetide is useful in treating inflammatory conditions not produced by an immune response to antigens, but instead by exposure of the body to noxious, irritating or otherwise harmful substances or stimuli produced by chemicals, electromagnetic irradiation (e.g., sunburn) or other agents or processes.

DETAILED DESCRIPTION

The present invention relates to the treatment of disease conditions not mediated by IgE using Pentigetide.

In addition to Pentigetide, substituted or otherwise derivatized forms of Pentigetide are also within the scope of the present invention. Preferred substituents include N-alpha acyl substituents at the amino terminus of Pentigetide of the form RCO—, where R is alkyl, alkenyl or alkynyl (either unbranched or branched, and preferably from 1 to about 8 carbons), or aryl, alkaryl, aralkyl or cycloalkyl (preferably of from about 6 to about 18 carbons); C-terminal substituents of the form —NHR$^1$ or —NR$^{12}$ (where each R$^1$ is independently hydrogen, alkyl, alkenyl or alkynyl (preferably of from 1 to about 8 carbons), or aryl, alkaryl, aralkyl or cycloalkyl (preferably of from about 6 to about 18 carbons); and C-terminal substituents of the form —OR (where R is as defined above). An amino-terminal acetyl substituent is a particularly preferred substituent. Pharmaceutically acceptable acid or base addition salts of Pentigetide are also contemplated herein.

Pentigetide and its derivatives as described above may be used in the treatment of various inflammatory disease conditions initiated by biological systems or pathways other than IgE. Particular examples of such non-IgE-mediated disease conditions are noted above in the discussion of Type II, III and IV hypersensitivity responses, and include a broad range of inflammatory conditions that are substantially non-allergic (non-type I hypersensitivity), i.e., non-IgE-mediated, in nature. Additional examples of such disease conditions are discussed in U.S. Pat. No. 4,628,045, the disclosure of which is incorporated herein by reference, and are contemplated to be within the scope of the present invention. By way of further example, the breadth of the present invention is illustrated by the fact that Pentigetide is useful in inhibiting inflammation mediated by the arachidonic acid pathway, which is invoked in a wide variety of allergic and non-allergic disease conditions. Thus, inflammatory diseases which involve in substantial part non-IgE-mediated mechanisms, even if in contribution with IgE-mediated mechanisms, may be expected to be inhibited or prevented to an enhanced degree by virtue of the activity of Pentigetide against one or more disease-contributive non-IgE-mediated disease mechanisms.

The following examples and the disclosure of U.S. Patent Application Serial No. 939,927 demonstrate the utility of Pentigetide in treating such non-IgE-mediated inflammatory disease conditions.

EXAMPLE 1: PENTIGETIDE INHIBITION OF TYPE IV HYPERSENSITIVITY

Type IV hypersensitivity (delayed-type hypersensitivity or DTH), as previously described, is triggered primarily by T cells having specialized T cell receptors able to recognize and bind to the specific sensitizing antigen on a cell's surface. Upon reexposure to an antigen, T cell receptor molecules bind to the antigen and trigger a complex series of events that result in secretion of lymphokines and other regulatory molecules that recruit new cells leading ultimately to the destruction of the antigen-bearing cell.

DTH may be readily induced in animals by the appropriate exposure of animals to sensitizing antigens known to elicit a DTH response. Lagrange, P. H., et al., J. Exp. Med. 139:528 (1974). In order to assess the effect of Pentigetide in suppressing the inflammation of DTH, two antigens were used. The first antigen, tetanus toxoid, is a chemically modified derivative of the tetanus toxin molecule. Tetanus toxoid was selected because it represents a single molecule that has few regions that act as antigens in a DTH response. The second antigen used to induce DTH was sheep erythrocytes, including the entire red blood cell which contains many different molecules which may simultaneously be recognized as antigens for T cells during the DTH response.

Tetanus toxoid-induced DTH reactions were elicited in approximately 60-day-old female Balb/C mice by injecting 25 mcg of tetanus toxoid (Mass. Dept. of Public Health, Lot No. LP 457 PR) subcutaneously in a 0.7 ml volume of saline containing 35.7 mcg tetanus toxoid/ml distributed between three dorsal injection sites at the beginning of each experiment (day "0").

Either saline or various amounts of Pentigetide were then injected in 0.2 ml volumes at the nape of the neck on day 3, 4 and 5 after tetanus toxoid immunization. A "positive control" substance, indomethacin, was also administered on day 4.

On day 5, the right hind footpad of mice was challenged with 0.057 mg tetanus toxoid in a volume of 0.025 ml. The left hind footpad was uninjected and served as a control. Approximately 24 hours later, the mean footpad volumes for injected ("challenged") and uninjected ("control") footpads were measured using a Buxco plethysmograph and compared. Evaluation of inflammation inhibition for Pentigetide or indomethacin was performed by calculating the percent change of the mean difference in volume of the challenged footpad versus the control footpad from drug or saline-injected mice. In these experiments, 97 mice served as saline-injected controls. The number of mice at each dose group is designated by n.

| Pentigetide Dose (mg/kg) | Percent Inhibition |
| --- | --- |
| 1.0 (n = 25) | 7 |
| 2.0 (n = 25) | 14 |
| 4.0 (n = 31) | 20 |
| 20.0 (n = 31) | 19 |
| 50.0 (n = 10) | 40 |

In the second test, sheep erythrocyte (SRBC)induced DTH reactions were elicited in approximately 60-day-old female Balb/C mice by injecting 0.2 ml of a 0.01% suspension of SRBC intravenously in the tail vein at the beginning of each experiment (day "0"). Either saline or various amounts of Pentigetide were then injected in 0.2 ml volumes at the nape of the neck on day 2, 3 and 4 after SRBC immunization. A "positive control" substance, indomethacin, was also administered on day 4.

On day 4, the right hind footpad of mice were challenged with 0.025 ml of a 20% SRBC suspension. The left hind footpad was uninjected and served as a control. Approximately 24 hours later, the mean footpad volumes for injected ("challenged") and uninjected ("control") footpads were measured using a Buxco plethysmograph and compared. Evaluation of inflammation inhibition for Pentigetide or indomethacin was performed by calculating the percent change of the mean difference in volume of the challenged footpad versus the control footpad from drug or saline-injected mice. The number of mice at each dose group is designated by n.

| Pentigetide Dose (mg/kg) | Percent Inhibition |
| --- | --- |
| 1.0 (n = 21) | 8 |
| 10.0 (n = 22) | 19 |
| 100.0 (n = 55) | 23 |
| 400.0 (n = 30) | 36 |
| 800.0 (n = 29) | 41 |

The higher dose of Pentigetide needed to provide substantial DTH inhibition is a reflection of the difference in the nature of the antigens used to elicit the DTH response. This dose difference illustrates that the dose of Pentigetide needed to inhibit DTH in human disease may vary greatly depending on the nature of the antigens involved in the DTH response. For example, sheep erythrocytes are intact cells and as such present the immune system with many varied structures that may act as sensitizing antigens including many proteins, complex carbohydrates, lipids and molecules that are conjugates of proteins, carbohydrates and lipids. Tetanus toxoid, by contrast, is a single protein molecule and therefore contains only a few structures able to act as antigens under the experimental conditions employed in these examples. It is to be expected, therefore, that the amount of Pentigetide needed to suppress the inflammation produced by these two antigens would differ, as the data presented suggests.

It is similarly expected that the dose of Pentigetide needed to provide a therapeutic effect in the treatment of non-allergic diseases of conditions (e.g., autoimmune diseases or other types of hypersensitivity conditions) may substantially vary depending on the disease or condition, stage of disease, route of Pentigetide administration and other factors. Indeed, the dose response curve associated with the non-IgE-mediated inflammatory inhibition of Pentigetide may in some cases be complex, although routine experimentation with various doses and systems can be expected to yield therapeutically effective doses.

EXAMPLE 2: PENTIGETIDE INHIBITION OF CARRAGEENAN-INDUCED EDEMA

Carrageenan is a sulphated polygalactan compound derived from certain algae that is widely used as an inflammatory-inducing agent in experimental animal models of inflammation (Thomson, A. W., et al. Agents and Actions, 11:265, 1981). By contrast to tetanus toxoid, SRBC and other inflammation-producing agents, carrageenan does not produce inflammation by the elicitation of an antigen-specific immune response towards itself.

Instead, the inflammatory reaction induced by carrageenan is produced by the non-specific activation of many inflammatory pathways including: complement, clotting, kinin, prostaglandin, leukotriene and superoxide production systems. Activation of these inflammatory pathways is simultaneously accompanied by the release of preformed inflammatory mediators such as histamine and serotinin. Additionally, carrageenan is selectively toxic to macrophages causing them to release cytotoxic and inflammatory proteases and other substances from disrupted lysosomes (Baker, K. C., et al., Fd. Chem. Toxic 24:891, 1986; Crunkhorn, P., et al. Br. J. Pharmac. 42:392, 1971).

The ability of carrageenan to activate the complement inflammatory system and many other inflammatory pathways resembles the broad activation that occurs in types II and III hypersensitivity in which complement activation plays a principal role in inducing inflammation. Activated complement, for example, like carrageenan, can rapidly cause cell lysis and cytotoxicity while simultaneously activating a broad range of additional inflammatory pathways.

In order to examine the ability of Pentigetide to inhibit carrageenan-induced inflammation, female Balb/C mice were injected with 0.025 ml of 1.0% carrageenan solution (type 1x carrageenan: Sigma No. C-1013, Lot No. 86F-0698) or saline in the right hind footpad 5 minutes after intravenous tail vein injection of 0 2 ml Pentigetide (1.0 mg/kg) or saline solution Indomethacin (10 mg/kg was used as a positive control and was administered by subcutaneous injection 24 hours prior to carrageenan injection. Footpad volumes were measured using a Buxco plethysmograph over a 6 hour period Pentigetide produced substantial inhibition of carrageenan-induced inflammation when compared to saline control animals.

| Hours After Carrageenan Injection | Percent Inhibition | |
| --- | --- | --- |
| | Pentigetide (1.0 mg/kg) | Indomethacin (10 mg/kg) |
| 1.0 | −2 | −35 |
| 2.0 | −51 | −60 |
| 4.0 | −19 | −39 |
| 6.0 | −34 | −47 |

These surprising findings indicate that Pentigetide can suppress the inflammation produced by activation of the complement system and the other inflammatory pathways activated by carrageenan. Since complement activation is a principal component of inflammation produced during type II and type III hypersensitivity reactions, Pentigetide can have an important therapeutic effect in diseases having hypersensitivity types II and III as components of their pathogenesis.

EXAMPLE 3: PENTIGETIDE INHIBITION OF NON-ALLERGIC URTICARIA

Conventional "allergic" urticaria is an IgE-mediated condition that is usually self-limiting. It represents a temporary allergic response to drugs, foods, infection or exposure to environmental conditions such as cold, heat, pressure or light. Allergic urticaria requires the combination of an antigen and IgE to mediate the release of histamine from basophils and mast cells. The histamine triggers vasodilation and increased vascular permeability as well as an axon reflex that increases swelling. Chronic refractory idiopathic urticaria (CRIU) is a non-allergic condition commonly known as "hives". Its symptoms include pruritis (itching) and the appearance of erythematous skin elevations and lesions. In contrast to allergic urticaria, it is not traceable to a particular etiologic agent and is not self-limiting (the designation "chronic" generally being given when the urticaria persists for more than six weeks). CRIU is not IgE mediated, and patients who suffer from the condition frequently display normal levels of IgE. Existing therapy for CRIU is merely supportive. Antihistamines such as hydroxyzine (Atarax), cyproheptadine (Periactin) and diphenhydramine (Benadryl) are used for the relief of pruritis but such agents have little effect on the appearance of the lesions. Other treatments include the use of steroids in severe cases; however, the risks associated with longterm steroid administration restrict any such therapy. Moreover, some patients are unresponsive to both antihistamines and steroid, leaving no specific therapy available to them until the present invention. Kaplan, A. P., in *Allergy: Principles and Practice*, eds. Middleton, E., et al., 2d ed. (Mosey Co., St. Louis: 1983), p. 1341.

Clearly, existing methods of treating the non-IgE mediated condition of CRIU are not satisfactory. It is one surprising discovery of this invention that when Pentigetide is administered in therapeutic doses, it may provide an effective treatment for CRIU. Thus, the therapeutic administration of Pentigetide to patients suffering from CRIU may significantly relieve the discomfort associated with those conditions in the absence of any known side-effects.

Two female patients (A and B) with chronic idiopathic urticaria were selected for treatment with Pentigetide on a compassionate need basis. The selection was based on the presence of non-allergic (non-IgE-mediated) urticaria uncontrolled by tolerated doses of antihistamines and the absence of any other known diseases. The patients, whose urticaria was so severe as to interfere with their normal activities and work, wished to avoid the addition of corticosteroids to their treatment regime. Prior to the treatment, the patients signed approved consent forms and FDA approval was obtained. The doses were prepared from 50 mg of lyophilized Pentigetide reconstituted into one ml water immediately before each subcutaneous injection.

Patient A, a 57 year old caucasian female with chronic idiopathic urticaria of unknown etiology, did not respond to maximum doses of H1 and H2 antagonists. Prior to Pentigetide treatment, as described here, she had 30 to 40 severely itchy hives per day. The disfigurement and discomfort associated with her urticaria significantly interfered with her daily activities. She received 50 mg of Pentigetide subcutaneously in each arm (total dose: 100 mg) on a Monday, Wednesday and Friday basis for a total of six treatments over two weeks. Preceding the Pentigetide treatment, she had been maintained on a combination of 50 mg Atarax 4 times a day and 300 mg cimetadine 4 times a day; this treatment continued during the Pentigetide treatment. Forty-eight hours after initial Pentigetide therapy, A's hives decreased to 5-10 per day and remained at that level throughout the two week period. Patient A also suffered from severe seasonal allergic rhinitis which totally resolved within 24 hours of initial Pentigetide therapy and remained in remission throughout the treatment. There was no experience of adverse side effects throughout the two week treatment, however, the urticaria re-evolved after Pentigetide was discontinued.

Patient B, a 62 year old caucasian female, suffered for 17 years from chronic idiopathic urticaria unresponsive to conventional antihistamine therapy She was seen at both the National Institute of Heath and the Mayo Clinic without therapeutic success. Her condition was controlled only through the use of moderate to high doses of corticosteroids which still left the hives nodular and highly pruritic. Antihistamines provided no therapeutic value. Prior to Pentigetide treatment, she was maintained on 1.5 mg Decadron every other day. With that treatment, her hive count was greater than 100 a day.

Patient B's Pentigetide treatment was identical to that of Patient A. Within 24 hours of treatment with Pentigetide, she experienced marked improvement. After two days of therapy, her hive count was reduced to less than 10 per day with an almost total resolution of pruritis. On the sixth day of Pentigetide injections, there was no more evidence of nodular urticarial lesions although a patch of fine, maculopapular rash remained on her right flank. She did not experience any side effects from the treatment and reported that she had never shown such a dramatic improvement in her condition except with high doses of corticosteroids. Following this improvement, Patient B's treatment was continued at 100 mg subcutaneously twice, rather than three times, a week for another two weeks, followed by a reduction to 50 mg twice per week. Total relief for the urticaria continued at this level.

In the practice of the methods of the present invention, an effective amount of Pentigetide or a derivative thereof, or a pharmaceutical composition containing the same, as defined above, is administered via any of the usual and acceptable methods known in the art, either singly or in combination with other compound or compounds of the present invention or other pharmaceutical agents such as antihistamines, corticosteroids, and the like. These compounds or compositions may thus be administered orally, sublingually, topically (e.g., on the skin or in the eyes), rectally (e.g , by suppository or foam), parenterally (e.g., intramuscularly, intravenously, subcutaneously or intradermally), or by inhalation, and in the form of either solid, liquid or gaseous dosage including tablets, suspensions, and aerosols as discussed in more detail hereinafter. The administration can be conducted in single unit dosage form with continuous therapy or in single dose therapy ad libitum.

In one preferred embodiment, the method of the present invention is practiced when the relief of symptoms is specifically required or perhaps imminent; in another preferred embodiment, the method hereof is effectively practiced as continuous or prophylactic treatment.

In view of the foregoing as well as in consideration of the degree of severity of the condition being treated, age of subject, and so forth, all of which factors being determinable by routine experimentation by one skilled in the art, the effective dosage in accordance herewith can vary over a wide range. A preferred dosage in humans, depending on the disease in question, may vary from about 0.5 to 50 mg/kg, while a possible range of necessary doses may vary from about 0.1 to 800 mg/kg.

Useful pharmaceutical carriers for the preparation of the compositions hereof, can be solids, liquids or gases; thus, the compositions can take the form of tablets, pills, capsules, powders, enterically coated or other protected formulations (such as binding on ion exchange resins or other carriers, or packaging in lipid protein vesicles) sustained release formulations solutions (e.g., ophthalmic drops), suspensions, elixirs, aerosols, and the like. The carrier can be selected from the various oils including those of petroleum, animal, vegetable or synthetic origin, for example, peanut oil, soybean oil, mineral oil, sesame oil, and the like. Water, saline, aqueous dextrose, and glycols are preferred liquid carriers, particularly (when isotonic) for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin Such compositions will, in any event, contain an effective amount of the active compound together with a suitable amount of carrier so as to prepare the proper dosage form for proper administration to the host.

To be effective for the prevention or treatment of inflammatory diseases it is important that the Pentigetide compound be relatively non-toxic, non-antigenic and non-irritating at the levels in actual use.

The present Pentigetide compounds may be synthesized by the solid phase peptide synthesis method, as described for example in Merrifield, J. Am. Chem. Soc., 85, 2149–2154 (1963); Meienhofer in "Hormonal Proteins and Peptides," ed. C. H. Li, Vol. 2 (Academic Press, 1973), pp. 48–267; and Barany and Merrifield in "The Peptides," eds. E. Gross and J. Meienhofer, Vol. 2 (Academic Press, 1980), pp. 3–285.

Exemplary solid phase methods for synthesizing such compounds are given in U.S. patent application Ser. No. 939,927 and are not repeated here In particular, methods for preparation of substituted Pentigetide compounds as disclosed herein are also given in that patent.

It is understood that various other modifications will be apparent to and can readily be made by those skilled in the art without departing from the scope and spirit of this invention. Accordingly, it is not intended that the scope of the claims appended hereto be limited to the description as set forth above, but rather that the claims be construed as encompassing all the features of patentable novelty which reside in the present invention, including all features which would be treated as equivalents thereof by those skilled in the art to which this invention pertains.

I claim:

1. A method for the treatment of non-IgE-mediated inflammatory disease conditions comprising administering to a mammalian subject a therapeutically effective amount of a peptide having the amino acid sequence Asp-Ser-Asp-Pro-Arg.

2. A method for the treatment of non-IgE-mediated inflammatory disease conditions comprising administering to a mammalian subject a therapeutically effective amount of a derivatized peptide comprising the amino acid sequence Asp-Ser-Asp-Pro-Arg formed with pharmaceutically acceptable N-alpha acyl substituents of the form RCO-(where R is an unbranched or branched lower alkyl, alkenyl or alkynyl group of from 1 to about 8 carbons, or an aryl, alkaryl, aralkyl or cycloalkyl group of from about 6 to about 18 carbons), or pharmaceutically acceptable C-terminal substituents of the form $-NHR^1$, $-NR^1_2$ or $-OR$ (where each $R^1$ is independently hydrogen, lower alkyl, alkenyl or alkynyl, as defined above, or aryl, alkaryl, aralkyl or cycloalkyl, as defined above, and R is as defined above) and including pharmaceutically acceptable salts of said derivatized peptides.

3. The method of claim 2 wherein said RCO-substituent is an acetyl substituent.

4. The method of claims 1, 2 or 3 wherein said non-IgE-mediated disease condition is a delayed-type hyersensitivity condition.

5. The method of claims 1, 2 or 3 wherein said non-IgE-mediated disease condition is an autoimmune disease.

6. The method of claims 1, 2 or 3 wherein said non-IgE-mediated disease condition is in substantial part a Type II hypersensitivity disease condition.

7. The method of claims 1, 2 or 3 wherein said non-IgE-mediated disease condition is in substantial part a Type III hypersensitivity disease condition.

8. The method of claims 1, 2 or 3 wherein said non-IgE-mediated disease condition is in substantial part a Type IV hypersensitivity disease condition.

9. The method of claims 1, 2 or 3 wherein said non-IgE-mediated disease condition is chronic refractory idiopathic urticaria.

10. A method of treating a non-IgE-mediated inflammation condition comprising administering to a mammalian subject a therapeutically effective amount of peptide or derivatized peptide of claims 1, 2 or 3 for the treatment of said non-IgE-mediated inflammation condition.

* * * * *